United States Patent [19]

Ohashi et al.

[11] 4,385,190
[45] May 24, 1983

[54] PROCESS FOR THE PRODUCTION OF DIETHERS

[75] Inventors: Yu Ohashi; Norio Sone; Takashi Tobita, all of Ichihara, Japan

[73] Assignee: Nisso Petrochemical Industry Company Limited, Tokyo, Japan

[21] Appl. No.: 262,127

[22] Filed: May 11, 1981

[30] Foreign Application Priority Data

May 27, 1980 [JP] Japan .................................. 55-69676

[51] Int. Cl.³ ............................................ C07C 41/02
[52] U.S. Cl. .................................... 568/603; 568/613; 568/608; 568/609; 568/614; 568/648; 568/644; 568/676; 568/672; 568/662; 252/364
[58] Field of Search ............... 568/613, 608, 609, 614, 568/648, 644, 676, 672, 603, 662

[56] References Cited

U.S. PATENT DOCUMENTS 4,146,736 3/1979 Scheffel et al. ................. 568/613 X

OTHER PUBLICATIONS

The Condensed Chemical Dictionary, (1971), 515.

Primary Examiner—Bernard Helfin
Attorney, Agent, or Firm—George B. Oujevolk

[57] ABSTRACT

A process for the production of a mono- or poly-alkylene glycol diether which consists of reacting an ether having at least one lower alkyl group with alkylene oxide in the presence of a heteropoly acid or a heteropoly acid acidic salt. Heteropoly acids and their acidic salts whose ratio of the hetero and coordinate atom is 1:6 and 1:12 are preferably used.

1 Claim, No Drawings

PROCESS FOR THE PRODUCTION OF DIETHERS

DETAILED EXPLANATION OF THE INVENTION

This invention relates to a process for the production of mono-or polyglycol diethers, particularly to a process for the production of mono-or poly-glycol diethers by insertion of alkylene oxides into ethers in the presence of a heteropolyacid.

Mono-or poly-glycol diethers are conventionally used for solvents such as the polar solvents having no active hydrogen atom for polymerization reaction and another various reactions. Further, their usage ranges widely from solvents for metals or non-metal hydrides or acidic gas adsorbents to polymerization catalyst components. Processes for preparing these glycol diethers are roughly classified into two groups: indirect methods such as Williamson's and its improved methods and hydrogenation of glycol ether formal, and direct methods such as insertion of alkylene oxide into an ether in the presence of a Lewis acid, mentioned in the Japanese Open Patent No. 34709/1978 (hereinafter referred to as JOP).

This invention relates to an improved direct methods mentioned above. Compared with the indirect methods, the direct ones can produce objective mono-or poly-glycol diethers economically by only one step. However, when a Lewis acid mentioned in the JOP is employed in this reaction, many serious disadvantages occur, for examples, in case of metal halides, they usually by-produce some glycol monoether halides which are not only hard to separate from the desired products, but also bad for the polymerization solvent or components of catalysts.

Another disadvantage is that gaseous halides or their etherate having a boiling point approximately corresponding to that of the desired product are very difficult to separate from each other. Furthermore, in general, Lewis acids mentioned in the JOP have a defect concerning inability of their recovery and re-use by neutralizing them prior to post-treatment of the reaction mixture and various problems such as by-production of resin-like polymers and corrosion of materials of equipment. For these reasons, Lewis acid catalysts mentioned in the JOP are not preferable for industrialization desirable for industrial use.

The inventors have investigated various catalysts having no such disadvantages other than Lewis acids mentioned in the JOP and found that the object of this invention was capable of being easily fulfilled by applying heteropoly acids, being protonic acids, to this reaction to carry out this invention. In other words, this invention is characterized by reacting an ether compound having lower alkyl groups with an alkylene oxide in the presence of a heteropoly acid and/or its acidic salt to produce alkylene glycol diethers.

Heteropoly acid and its salts had not usually been employed for industrial use except only as reagents in a laboratory. Recently, however, there have been some examples they were applied to alkylation with olefin, isomerization of olefin or preparation of ester from alcohols. The heteropoly acids and their acidic salt are distinguished from solid-acid due to strong acids, having no acid strength distribution, easy solubility in water or organic solvents and having an oxidation-reduction-ability and a lot of crystal water. Furthermore, the heteropoly acids and their acidic salts are also distinguished from sulfuric, chloric or phosphoric acid which are usually classified into strong protonic acid, moreover, they have no catalitic activities in this reaction. Therefore, heteropoly acids and their acidic salts are recognize as a new catalyst for this direct method reaction. Its reaction mechanism, however, has not been discovered as yet.

When heteropoly acids and/or their acidic salts are employed in this reaction, high reactivities are obtained and many problems of manufacturing are solved which the usual catalyst did not accomplished, for examples, by-products such as charcoal or resin-like are not produced in spite of their strong acidities, since they are extremely stable to water and heat so as to be capable of being recovered and re-used even after thermal hysteresis at distillation, being capable of re-activating with acids for heteropoly acids and their salt which are neutralized prior to distillation, and having favorable properties against corrosion.

Generally known heteropoly acids and their acidic salts whose ratio of the hetero and coordinate atom is 1:6 to 1:12 may be widely used in this invention. In further detail, the hetero atom of a heteropoly acid is selected from boron, silicon, phosphorus, chromium, germanium, titanium, manganese, iron, cobalt, arsenic and the like, and a poly atom (coordination atom) of an acidic group which coordinates with condensation by sharing an oxygen covalently to the hetero atom is one of molybdenum, tungsten, vanadium, niobium and a mixture of these atoms. The heteropoly acid, or salt thereof, may thus be selected from the group consisting of molybdic acid, tungstic acid, vanadic acid, niobium acid or a mixture thereof coordinated with a hetero atom selected from the group consisting of boron, silicon, phosphorus, chromium, germanium, titanium, manganese, iron, cobalt and arsenic, and a mixture thereof.

The heteropoly acid acidic salts is a metal salt made by substituting a part of protons on a heteropoly acid with a metal cation or an amino salt obtained by neutralizing a heteropoly acid with an organic base such as ammonia or an amine, the metal salt being more preferable. The metal cation used in this invention is one which generally forms a neutralized salt with an acid. Favorable examples of the metal cation include alkali and alkaline-earth metals, copper, silver, cobalt, nickel, zinc, cadmium, aluminum, tin and manganese. "Kagaku Daijiten", vol. 8, p 339- (Kyoritsu Publishing Co., 1972 edition) describes extents and chemical structures of the heteropoly acids and their acidic salts in detail which this invention should refer to.

Preferable heteropoly acids and their acidic salts of this invention are those whose ratio of the hetero to coordination atom is 1:12. Representative examples of the heteropoly acid are dodecamolybdophosphoric acid, dodecamoylbdosilicic acid, dodecamolybdotitanic acid, dodecamolybdoarsenic acid, dodecamolybdogermanic acid, dodecatungstophosphoric acid, dodecatungstosilicic acid, dodecatungstoboric acid, dodecatungstotitanic acid, dodecatungstoarsenic acid, dodecatungstoferric acid, dodecatungstocobaltic hydroxide, dodecatungstomolybdophosphoric acid, dodecamolybdo-vanadophosphoric acid, dodecamolybdovanadosilicic acid and dodecatungsto-vanadosilicic acid, and heteropoly-acid acidic salts include disodium dodecamolybdosilicate, calcium dodecatungstosilicate, dimanganese dodecamolybdophosphate, nickel dodecamolybdophosphate, copper dodecamolybdophosphate. Heteropoly acids and their acidic salts whose hetero atom is boron, silicon, phosphorus or germanium and whose coordinate atom is molybdenum or tungsten are particularly favorable to the use.

The heteropoly acids and their acidic salts of this invention have a lot of crystal water in addition to structural-water, the former being possible to be removed by heat treatment. Generally, changes of quantities of crystal water influence on activity of catalysts. However, this invention allows water to exist widely, ranging from anhydrides to 16 to 29 molecules of crystal water or further to 50 molecules of free water. Reaction rates are somewhat slow when anhydrides are used, on the contrary, the existence of a lot of free water is unfavorable, resulting in increasing reaction by-products with alkylene oxides. Therefore, preferable water content ranges from anhydrides to maximum volume of crystal water and to 20 molecules as free water.

A wide range of lower alkyl ethers may be employed as a starting ether according to the present invention. Particularly preferable compounds are shown in the general formula (I):

(I)

(wherein $R^1$ is methyl or ethyl group; $R^2$ is selected from the group of straight chain alkyl group having 1 to 12 carbon atoms, substituted with alkoky or lower alkyl groups or unsubstituted phenyl group or an aralkyl group consisting in a phenyl and a lower alkylene group, m is an integer from 1 to 4 and n is an integer from 0 to 8. Sometimes n is shown as an average number when the starting material is a mixture of components whose n are different.

When n is 2 or more, m may be different. Representative examples of $R^2$ is methyl, ethyl, propyl, butyl, pentyl, hexyl, heptyl, octyl, nonyl, decyl, undecyl, dodecyl, phenyl, toluyl, xylyl, ethylphenyl, propylphenyl, cumyl, butylphenyl, benzyl, phenylethyl, phenylpropyl, phenylbutyl, methoxyphenyl, ethoxyphenyl, propoxyphenyl or buthoxyphenyl.

The reactivity of the starting ether of this invention tends to be more active when $R^1$ and $R^2$ have a smaller number of carbon atoms, and m and n are smaller integers. This fact seems to be generally based on basicity of the starting ether.

Representative examples of preferable starting ethers are dialkyl ethers such as dimethyl ether, diethyl ether, methyl ethyl ether, methyl propyl ether, methyl butyl ether, methyl pentyl ether, methyl hexyl ether, methyl decyl ether and methyl dodecyl ether; alkyl aralkyl ethers such as benzyl methyl ether; dialkyl formals such as dimethyl formal and diethyl formal; and alkylene glycol dialkyl ethers such as ethylene glycol diethyl ether, ethylene glycol methyl ethyl ether, 1,3-propylene glycol dimethyl ether and 1,4-butylene glycol dimethyl ether.

Various alkylene oxides may be used in this invention. Compounds shown in the general formulae (II) and (III) are particularly preferable:

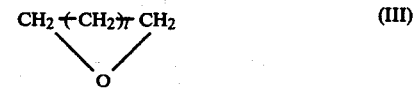

(wherein, $R^3$ is a hydrogen atom or unsubstituted or halogen-substituted alkyl group having 1 to 5 carbon atoms or a phenyl group)

(III)

(wherein, l is an integer from 1 to 5).

Preferable examples are ethylene oxide, 1,2-propylene oxide, 1,2-butylene oxide, epichlorohydrin, styrene oxide, trimethylene oxide, tetramethylene oxide, pentamethylene oxide and hexamethylene oxide. Ethylene oxide or epichlorohydrin is particularly preferable.

Embodiments of this invention are explained as follows: Water content in a heteropoly acid or its acidic salt may be easily adjusted to the desired amount by adding a suitable quantity of water either directly to the catalyst or separately to the reaction system in the case of shortage, and by dehydrating by means of heating to 100°–500° C. under reduced or atmospheric pressure in the case of excess.

The heteropoly acids or their acidic salts can be used in their natural state or by employing carriers such as silica, alumina or activated carbon for advantages in the reaction methods, post-treatment of reaction mixtures and separation of the catalyst.

This invention may be a carried out continuously or discontinuously, at a liquid-or gas-phase. The fixed bed method may also be adopted advantageously because heteropoly acids and their acidic salts can be used in the form of being supported by a carrier.

It is advantageous to carried out the reaction, including dissolution of raw materials and removal of reaction heat, in the presence of a reaction medium which is inert to catalysts, reactants and products. Such inert solvents are, for example, dichloromethane, nitromethane, chlorobenzene, benzene, ethyl acetate, dioxane or reaction products of alkylene glycol diethers. The reaction may preferably be carried out under an inert gas such as, for example, nitrogen or helium for safety, maintaining of activity of catalyst and preventing of extraordinary reactions.

The reaction temperature is preferably 0° to 200° C. The pressure, depending on reaction methods used, may be sufficient at the pressure and temperature of the reaction system employed. If necessary, the desired pressure may be adjusted by using an inert gas.

The reaction rate depends on the types and concentrations of the heteropoly acids or their acidic salts, reaction temperatures, types and concentrations of starting ethers and alkylene oxides, and if used, types and quantity of solvents. The desired results, can be obtained by combining the factors and levels mentioned above adequately.

The amount of the heteropoly acid and/or its acidic salt according to this invention is 0.1–50% by weight to the starting ether, particularly 1–20% by weight being preferably used. In the case of a fixed-bed reaction or continuous operation, a contact rate of a starting diether may be adopted 0.01 to 10 parts by weight to one part by weight of the heteropoly acid and/or its acidic salt.

The reaction mixtures obtained according to this invention is a mixture of alkylene glycol diethers having distribution relates to the polymerization degree of oxyalkylene groups. The composition may be con- TABLE 3-continued

| example No. | heteropoly acid | conversion (%) $CH_3OCH_3$ | $\underset{O}{CH_2\text{—}CH_2}$ | selectivity (based on ethylene oxide) (%) | | | | | | | | | | 1,4-dioxane | others (Note) |
|---|---|---|---|---|---|---|---|---|---|---|---|---|---|---|---|
| | | | | $CH_3O\text{(}CH_2CH_2O\text{)}_{\overline{n}}CH_3$ composition (%) | | | | | | | | | | | |
| | | | | n = 1 | 2 | 3 | 4 | 5 | 6 | 7 | 8 | 9 | total | | |
| 7 | acid tetrahydrate dodecamolybdophosphoric acid monohydrate | 44.9 | 99.2 | 29.5 | 18.4 | 10.5 | 6.8 | 3.8 | 2.9 | 0.8 | 0.3 | — | 73.0 | 20.5 | 6.5 |
| 8 | dodecamolybdophosphoric acid triacontahydrate | 43.9 | 99.5 | 28.7 | 15.8 | 11.4 | 8.0 | 4.1 | 3.2 | 1.2 | 0.8 | 0.5 | 73.5 | 18.1 | 8.1 |

Note:
the same as mentioned in Table 1

EXAMPLE 9

3 g of sodium dodecatungstosilicate pentahydrate and 20 g of monochlorobenzene were charged into an autoclave then 23 g of dimethy ether was introduced with cooling. 22 g of ethylene oxide was added with stirring at 50° C. within 15 minute, followed by a further 3-hour reaction at the same temperature. After completion of the reaction, the contents was cooled to room temperature and unreacted dimethy ether was collected to recover by cooling with dryice-methanol. The reaction mixture remained was analysed by gas chromatography to give the results shown in Table 4.

EXAMPLE 10

Into an autoclave, 3 g of manganese dodecatungustophosphate trihydrate and 20 g of dichloromethane were placed, and 23 g of dimethyl ether was introduced with cooling. Then, Example 9 was repeated. The reaction mixture obtained was analysed by gas chromatography to give the results shown in Table 5.

amount of ethylene oxide at 100° C. The results are shown in Table 6.

EXAMPLE 14

Into a four-necked flask equipped with a stirrer, a condenser, a thermomether and a dropping funnel were added 1 mole (90 g) of ethylene glycol dimethyl ether and 4 g of dodecatungstophosphoric acid tetrahydrate, and 0.5 moles (46.3 g) of epichlorohydrine was reacted with them at 50° to 60° C., then repeated treatment in a manner similar to that described in Example 1. The analysed results are shown in Table 7.

EXAMPLES 15 AND 16

Into a 500 ml autoclave equipped with a stirrer and a blowing tube for ethylene oxide, were added 40.0 g of monochlorobenzene as a solvent, 85.8 g of dimethyl ether, 5.8 g of dodecatungstosilicic acid treated with burning in an electric oven under the conditions given in Table 8 as a catalyst, then 82.0 g of ethylene oxide was reacted by dropping within the period of 2 hours with stirring at 40° C. at 5 kg/cm².G. The reaction continued for another one hour at the same temperature. After unreacted dimethyl ether was recovered, the product was analysed by gas chromatography to give the results shown in Table 8.

TABLE 4

| conversion (%) | | selectivity (based on ethylene oxide) (%) | | | | | | | | | | | | |
|---|---|---|---|---|---|---|---|---|---|---|---|---|---|---|
| $CH_3OCH_3$ | $\underset{O}{CH_2\text{—}CH_2}$ | $CH_3O\text{(}CH_2CH_2O\text{)}_{\overline{n}}CH_3$ composition (%) | | | | | | | | | | 1,4-dioxane | others (Note) |
| | | n = 1 | 2 | 3 | 4 | 5 | 6 | 7 | 8 | 9 | total | | |
| 43.7 | 97.5 | 28.6 | 18.7 | 11.6 | 7.2 | 3.1 | 2.2 | 1.5 | 0.3 | — | 73.2 | 20.1 | 6.7 |

Note:
the same as mentioned in Table 1

TABLE 5

| conversion (%) | | selectivity (based on ethylene oxide) (%) | | | | | | | | | | | | |
|---|---|---|---|---|---|---|---|---|---|---|---|---|---|---|
| $CH_3OCH_3$ | $\underset{O}{CH_2\text{—}CH_2}$ | $CH_3O\text{(}CH_2CH_2O\text{)}_{\overline{n}}CH_3$ composition (%) | | | | | | | | | | 1,4-dioxane | others (Note) |
| | | n = 1 | 2 | 3 | 4 | 5 | 6 | 7 | 8 | 9 | total | | |
| 44.6 | 98.8 | 28.0 | 19.2 | 12.4 | 8.6 | 4.4 | 1.4 | 0.5 | 0.2 | — | 74.7 | 19.0 | 6.3 |

Note:
the same as mentioned in Table 1

EXAMPLES 11 TO 13

Example 1 was repeated except for using various types and a weight of starting ethers and 4 g of various heteropoly acids shown in Table 6 to react with a fixed trolled by changing a molar ratio of a starting ether and an alkylene oxide.

In other words, the product is a mixture of alkylene glycol diethers in various degrees of polymerization for the oxyalkylene radical with statistic distribution. In order to obtain a mixture of homologs of a lower molecular weight the average ratio of an alkylene oxide to a starting ether should be decreased, and to obtain a higher one, the ratio should be increased. In a liquid-phase reaction, it is possible to conduct the reaction by changing the starting ether, an alkylene oxide, a heteropoly acid and/or its acidic salt, and if necessary solvents simultaneously. It is, however, preferable to add the alkylene oxide gradually to the reactor because of safety operation.

Generally, the reaction mixtures obtained through this invention may be purified by distillation with or without neutralization prior to the distillation to give the several desired uniformly-composed alkylene glycol diethers or their mixtures. Film distillation method is sometimes advantageous to distill the higher molecular weight mixtures. Sometimes an organic layer simply separated from the reaction mixtures by salting-out with alkaline-aqueous solution can be the desired products without distillation.

When the heteropoly acids and/or their acidic salts are employed in a insoluble forms, they may be recovered and re-used by separating with filtration from the reaction mixtures or distillation residue. On the other hand, when they are employed in an insoluble form into the reaction system, they may be re-used in the form of a distillation residue.

The present invention is explained in the following examples.

EXAMPLE 1

Into an autoclave 2 g of dodecatungstosilicic acid dihydrate ($SiO_2.12WO_3.2H_2O$) and 20 g of monochlorobenzene were charged together, then 23 g of dimethyl ether was introduced with cooling. 22 g of ethylene oxide was added within the period of 15 minutes with stirring at 50° C., followed by a further 3 hour reaction at the same temperature.

After completion of the reaction, and cooling to room temperature, unreacted dimethyl ether was collected to be recovered by cooling with dry ice-methanol. The reaction mixture remained was analyzed by gas chromatography to give the results shown in Table 1.

EXAMPLE 2

Example 1 was repeated except for using dodecatungstosilicic acid separated by filtration from the reaction mixture obtained in Example 1. The reaction mixture obtained was analysed by gas chromatography to give the results shown in Table 2.

EXAMPLES 3 TO 8

By using the same ratio of starting materials and similar reaction process, Example 1 was repeated except for changing types of dodecaheteropoly acids used. The reaction mixture obtained was analysed by gas chromatography to give the results shown in Table 3.

TABLE 1

| conversion (%) | | selectivity (based on ethylene oxide) (%) | | | | | | | | | | | |
|---|---|---|---|---|---|---|---|---|---|---|---|---|---|
| | $CH_2-CH_2$ | $CH_3O+CH_2CH_2O)_nCH_3$ composition (%) | | | | | | | | | | 1,4- | others |
| $CH_3OCH_3$ | \\ / O | n = 1 | 2 | 3 | 4 | 5 | 6 | 7 | 8 | 9 | total | dioxane | (Note) |
| 45.3 | 99.2 | 29.9 | 17.4 | 11.6 | 6.9 | 3.8 | 2.7 | 1.2 | 0.5 | 0.1 | 74.1 | 19.1 | 6.8 |

Note:
acetoaldehyde, mono-or poly-ethylene glycol monomethyl ethers and polyethylene glycols

TABLE 2

| conversion (%) | | selectivity (based on ethylene oxide) (%) | | | | | | | | | | | |
|---|---|---|---|---|---|---|---|---|---|---|---|---|---|
| | $CH_2-CH_2$ | $CH_3O+CH_2CH_2O)_nCH_3$ composition (%) | | | | | | | | | | 1,4- | others |
| $CH_3OCH_3$ | \\ / O | n = 1 | 2 | 3 | 4 | 5 | 6 | 7 | 8 | 9 | total | dioxane | (Note) |
| 44.5 | 99.0 | 29.9 | 16.6 | 10.4 | 6.7 | 3.9 | 2.9 | 1.5 | 0.8 | 0.2 | 72.9 | 20.2 | 6.9 |

Note:
the same as mentioned in Table 1

TABLE 3

| example No. | heteropoly acid | conversion (%) | | selectivity (based on ethylene oxide) (%) | | | | | | | | | | | |
|---|---|---|---|---|---|---|---|---|---|---|---|---|---|---|---|
| | | $CH_3OCH_3$ | $CH_2-CH_2$ \\ / O | $CH_3O+CH_2CH_2O)_nCH_3$ composition (%) | | | | | | | | | 1,4- dioxane | others (Note) |
| | | | | n = 1 | 2 | 3 | 4 | 5 | 6 | 7 | 8 | 9 | total | | |
| 3 | dodecatungstophosphoric acid dihydrate | 42.3 | 99.0 | 27.4 | 15.5 | 11.0 | 7.3 | 4.7 | 3.9 | 2.5 | 1.0 | 0.3 | 73.6 | 19.5 | 6.9 |
| 4 | dodecatungstoboric acid decahydrate | 42.8 | 99.5 | 27.0 | 16.9 | 11.5 | 7.3 | 4.4 | 3.6 | 1.8 | 1.1 | 0.6 | 74.2 | 18.8 | 7.0 |
| 5 | dodecatungstogermanic acid tetrahydrate | 43.6 | 98.8 | 28.7 | 17.3 | 10.7 | 6.5 | 3.8 | 2.8 | 1.4 | 0.9 | 0.3 | 72.4 | 20.8 | 6.8 |
| 6 | dodecamolybdosilicic | 42.3 | 99.3 | 26.9 | 16.4 | 11.1 | 7.3 | 4.4 | 3.8 | 2.3 | 0.9 | 0.4 | 73.5 | 19.7 | 6.8 |

TABLE 6

| example No. | (A) starting ether R—O—R' | (B) CH$_2$—CH$_2$ \ / O | (A)/(B) molar ratio | heteropolyacid | conversion (%) (A) | conversion (%) (B) | selectivity (based on ethylene oxide) (%) RO(CH$_2$CH$_2$O)$_n$R' total of n = 1, 2, 3 and >4 | 1,4-dioxane |
|---|---|---|---|---|---|---|---|---|
| 11 | CH$_3$O(CH$_2$)$_6$CH$_3$ 80 g | 18 g | 1.5 | dodecamolybdo-phosphoric acid dihydrate | 13.1 | 94.0 | 27.1 | 67.2 |
| 12 | CH$_3$OCH$_2$CH$_2$C$_6$H$_5$ 80 g | 13 g | 0.5 | dodecamolybdo-silicic acid tetrahydrate | 11.0 | 94.5 | 28.2 | 66.0 |
| 13 | CH$_3$OCH$_2$OCH$_3$ 80 g | 9 g | 5.0 | dodecatungsto-silicic acid monohydrate | 14.0 | 98.8 | 88.0 (Note) | 5.9 |

Note:
The product is represented by CH$_3$O(CH$_2$O)$_l$(CH$_2$CH$_2$O)$_n$—CH$_3$ and CH$_3$O(CH$_2$CH$_2$O)$_l$(CH$_2$O)$_j$(CH$_2$CH$_2$O)$_m$CH$_3$ (l + m = n) with ignoring the oder of (CH$_2$O) and (CH$_2$CH$_2$O).

TABLE 7

| conversion (%) | | selectivity (based on epichlorohydrine) (%) CH$_3$O(CH$_2$CH$_2$O)$_l$(CHCH$_2$O)$_m$CH$_3$ <br>                                               CH$_2$Cl <br> composition (%) (Note) | | | | | 2,5-dichloro-methyl-1,4-dioxane |
|---|---|---|---|---|---|---|---|
| ethylene glycol dimethyl ether | epichlorohydrine | n = 1 | 2 | 3 | >4 | total | |
| 35.2 | 98.0 | 61.4 | 16.8 | 5.0 | 0.9 | 84.1 | 11.0 |

Note:
The formula is represented with ignoring the order of
(CH$_2$CH$_2$O) and (CHCH$_2$O), similar to that in Example 13.
                          |
                         CH$_2$Cl

TABLE 8

| example No. | burning conditions | conversion (%) CH$_3$OCH$_3$ | conversion (%) CH$_2$—CH$_2$ \ / O | selectivity (based on ethylene oxide) (%) CH$_3$O(CH$_2$CH$_2$O)$_n$CH$_3$ composition (%) | | | | | | | | | | 1,4-dioxane | others (Note) |
|---|---|---|---|---|---|---|---|---|---|---|---|---|---|---|---|
| | | | | n = 1 | 2 | 3 | 4 | 5 | 6 | 7 | 8 | 9 | total | | |
| 15 | 300° C. 2 hours | 44.6 | 99.1 | 29.3 | 18.9 | 9.6 | 6.8 | 4.1 | 2.2 | 0.9 | 0.5 | 0.2 | 72.5 | 20.3 | 7.2 |
| 16 | 400° C. 4 hours | 31.9 | 99.2 | 18.5 | 11.4 | 8.7 | 7.9 | 6.5 | 5.0 | 3.2 | 2.6 | 1.8 | 65.6 | 28.7 | 5.7 |

Note:
the same as mentioned in Table 1

What we claim is:

1. A process for the production of mono- or polyalkylene glycol diethers which comprises:
reacting a lower alkyl ether with a lower alkylene oxide in the presence of a heteropoly acid or a salt thereof wherein
the heteropoly acid, or a salt thereof, is selected from the group consisting of molybdic acid, tungstic acid, vanadic acid, niobium acid or a mixture thereof coordinated with
a hetero atom selected from the group consisting of boron, silicon, phosphorus, chromium, germanium, titanium, manganese, iron, cobalt and arsenic, and a mixture thereof.

* * * * *